United States Patent [19]
Kempf

[11] Patent Number: 5,459,605
[45] Date of Patent: Oct. 17, 1995

[54] 3-D ENDOSCOPE APPARATUS

[75] Inventor: Paul S. Kempf, 120 Cerro St., Encinitas, Calif. 92024

[73] Assignees: Paul S. Kempf; Pilar Moreno Kempf Family Trust, both of Solana Beach, Calif.

[21] Appl. No.: 161,911

[22] Filed: Dec. 8, 1993

Related U.S. Application Data

[63] Continuation-in-part of Ser. No. 992,086, Dec. 17, 1992, abandoned.

[51] Int. Cl.$^6$ ....................................... H01J 40/14
[52] U.S. Cl. ..................... 359/462; 359/463; 359/466; 359/472; 359/476; 385/34; 385/117
[58] Field of Search ..................... 359/462, 463, 359/464, 465, 466, 471, 472, 476; 385/34, 117, 119

[56] References Cited

U.S. PATENT DOCUMENTS

| | | |
|---|---|---|
| 3,520,587 | 7/1970 | Tasaki et al. |
| 3,901,220 | 8/1975 | Koyasu et al. ........................ 128/6 |
| 4,111,529 | 9/1978 | Yamashita ........................ 359/753 |
| 4,623,223 | 11/1986 | Kemp ........................ 359/472 |
| 4,651,201 | 3/1987 | Schoolman ........................ 348/45 |
| 4,838,247 | 6/1989 | Forkner ........................ 128/6 |
| 4,862,873 | 9/1989 | Yajima et al. ........................ 359/462 |
| 4,926,257 | 5/1990 | Miyazaki ........................ 358/98 |
| 5,191,203 | 3/1993 | McKinley ........................ 359/480 X |

FOREIGN PATENT DOCUMENTS

WO9014040  11/1990  WIPO.

Primary Examiner—David C. Nelms
Assistant Examiner—Huan Hoang
Attorney, Agent, or Firm—Brown, Martin, Haller & McClain

[57] ABSTRACT

An endoscope has a first end for insertion into a body, or other visually obscured area, with an optical image-forming lens device in the first end for forming two, side-by-side images of an object on opposite sides of the central axis of the endoscope. The images are transmitted to the opposite end of the endoscope, where they are received by a viewing device for three-dimensional viewing of the images by an operator. An image converging mechanism is provided in the image paths to provide a suitable convergence angle between the images at the viewing device.

34 Claims, 5 Drawing Sheets

3-D ENDOSCOPE APPARATUS

CROSS-REFERENCE TO RELATED APPLICATION

This application is a Continuation-In-Part of Application Ser. No. 07/992,086 of the same Applicant, filed Dec. 17, 1992, now abandoned..

BACKGROUND OF THE INVENTION

The present invention relates generally to borescopes or endoscopes for viewing inaccessible areas which are not directly viewable by eye, and is particularly concerned with endoscope instruments as used in surgery and diagnostics to allow doctors to view regions inside the body through a relatively small incision.

Typical surgical endoscopes have an optical system combined with an elongate optical pathway or channel, which may be rigid or flexible, for transmitting an image formed at one end of the channel to the opposite end of the channel. Simple endoscopes have only one optical channel and create only a two-dimensional or monoscopic view of the region under inspection. This will lack depth perception, making it difficult to perform an accurate inspection or surgery. Thus, three-dimensional or stereoscopic endoscopes have been developed for creating a three-dimensional view of the object or region under inspection. These endoscopes are provided with a pair of optical paths or image guides for transmitting right- and left-hand images of the object to a stereoscopic viewer. The stereoscopic viewer has microscope-like eyepieces through which the surgeon views the respective images. The eyepieces are arranged so that the surgeon's eyes provide the necessary convergence to combine the images into a stereoscopic view. Stereoscopic endoscope systems of this type are described, for example, in U.S. Pat. No. 3,520,587 of Tasaki et al. and U.S. Pat. No. 4,651,201 of Schoolman.

One major disadvantage of the known stereoscopic endoscope systems is that the two parallel optical systems used in such arrangements cannot converge the images and will provide two separate images or video pictures where a video viewing system is used, the images having a large relative offset to the image center. Although the human brain can converge and "fuse" two separate views if the separation between the images is not too great, this is not easy or comfortable to achieve in practice. In typical stereo-microscopes, the problem is solved by using two converging optical systems.

Convergence of right eye and left eye images of an object is done in normal stereopsis by converging the optical axes with the eyes or optical/mechanical means to accomplish convergence of the right and left images so that the brain receives and perceives the images as sufficiently close together for the brain to combine (fusion) the images as a single three-dimensional image. In normal unaided vision, this is accomplished in Panum's Fusional Area and by optical/mechanical means the same result can be obtained at much shorter focal distances than the eyes can converge. The stereomicroscope is an example of such an optical/mechanical device. However, this is not a practical solution in endoscopes where the necessary convergence at very short focal lengths is compounded by the need to keep the overall diameter of the system as small as possible so that the endoscope tube can be inserted through a single minimum size surgical incision, minimizing invasive procedures. The optics of the endoscope must therefore be small enough to be enclosed in a single relatively small diameter tube.

SUMMARY OF THE INVENTION

It is an object of the present invention to provide a new and improved endoscope or borescope apparatus for providing a convenient, three-dimensional view of an object or region inside a body or other inaccessible areas which are not directly viewable by eye.

According to one aspect of the present invention, an endoscope apparatus is provided which comprises an elongate endoscope tube having a central longitudinal axis, a first end for insertion into a body and an opposite, second end which remains outside the body, an optical image forming device in the first end of the tube for forming two images of an object at a distance from the device from opposite sides of the central axis, the image forming device including a pair of optical surfaces each cut at an angle for directing the images into closely adjacent, parallel optical paths, an elongate optical transmission device extending through the tube for transmitting the images to the second end of the tube, the transmission device having a first end positioned to receive the image formed by the image forming device, and an opposite, second end, and a viewing device for receiving and viewing the two images.

In an alternative embodiment of the invention, the apparatus comprises an elongate endoscope tube having a first end for insertion into a body and a second end which remains outside the body, an optical image forming device in the first end of the tube for forming two images of an object on adjacent paths, an elongate optical transmission device having opposite first and second ends and extending through the endoscope tube from the image forming device for transmitting the images to the second end of the transmission device, a stereoscopic viewing device for receiving and viewing the images, and an interconnect optics assembly between the second end of the transmission device and the viewing device for adjustment of the separation between the images. In one embodiment of the invention, the interconnect optics assembly comprises a system of lenses focusing on the proximal or second end of the transmission device and transmits the images onto a sensor surface of the viewing device. The lenses are arranged to move the images into an overlapping position. This may be done by pivoting the lenses or moving them transversely so as to shift the images.

In an alternative arrangement, the interconnect optics is a single prism positioned in the path of one of the images from the transmission device, and movable towards and away from the second end of the transmission device. This movement will shift the image to the right or left relative to the other image. Prisms may be positioned in the optical paths of both images. As an alternative to one or more axially movable prisms, where space is limited between the transmission device and viewing device, a pair of counter-rotating prisms may be positioned in the pathway of one of the images.

Preferably, the viewing device comprises right and left video cameras which are mounted in the second end of the endoscope tube. The user may directly view the images via a direct viewing or eyepiece system. However, in the preferred embodiment of the invention, the outputs of the two video cameras are connected to a 3-D video viewing system, such as the stereo image display system described in my U.S. Pat. No. 4,623,223, the contents of which are incorporated herein by reference. In that system, stereo views of a scene are reflected by angled plano mirrors onto a concave mirror. The concave mirror focuses real images in planar registration in front of the concave mirror, so that the observer sees a separate stereo view in each eye. This allows the surgeon or doctor to "see" a three-dimensional video picture of the object without having to use an eyepiece device attached to the endoscope. This arrangement is therefore more convenient for the surgeon or technician.

The image forming device may comprise one or two gradient index or so-called GRIN lenses which have the property of forming a real image at their exit surfaces. This allows an image transmitting device such as a fiber-optic bundle to be connected directly to the exit face of each GRIN lens, or a GRIN rod-type lens itself may extend to the second end of the transmission device for forming and transmitting the image. In one example, two GRIN lenses are positioned parallel to one another on opposite sides of the central axis to form the two images. The angled or wedge faces may be formed directly on the end faces of the lenses, with the longest longitudinal dimensions of the lenses directly adjacent to one another at the central axis of the device. In another alternative, the GRIN lenses may have flat end faces and a double wedge prism may be positioned with its flat face abutting the end faces of the lenses and its apex positioned on the central axis of the endoscope. Alternatively, a single GRIN lens may be positioned with its central axis coincident with the central axis of the endoscope, the end of the lens having a double wedge shape with a pair of angled faces or bevels converging to a point on the central axis. Instead of providing angled faces on the end of the single GRIN lens, the GRIN lens may have a flat end face with a double wedge prism cemented to the flat end face so that the apex of the prism lies on the central axis of the assembly. In another alternative, a spherical lens surface covers both imaging lenses.

In each of these cases, the angles of the surfaces are determined by the convergence angle for a predetermined working distance. The angled surfaces or spherical lens surfaces converge the two images so that their optical axes coincide at the predetermined working distance.

In an alternative arrangement, two GRIN lenses may be oriented at an angle, and the optical transmission device may comprise a pair of parallel fiber-optic bundles having end faces cut at the same angle and abutting the angled ends of the respective lenses.

In another embodiment of the invention, the image forming device comprises a single refractive objective lens centered on the central axis of the endoscope, and two prisms are located at or near the exit face of the lens to divide it into two halves, the prisms abutting on the central axis to diverge the optical axes of the two halves of the lens so that they are parallel to one another.

Instead of having lens surfaces which must be ground to an angle, which is more complex and costly for manufacturing purposes, the endoscope may have two lenses such as GRIN lenses at the first end which each have a single flat planar surface at their outer or distal ends and a flat planar surface on which the GRIN lens image is formed on the inner proximal surface. The proximal surface of the GRIN lens abuts and is cemented to the distal end of a fiber-optics bundle or transmission device, which transmits the image to the proximal end of the fiber-optics bundle where it is viewed by the interconnect optics assembly. Preferably, the interconnect optics assembly comprises a pair of pivotally mounted lenses each positioned between a respective one of the transmission devices and the viewing device so as to focus on the end of the respective transmission device and angled so as to shift the center of the image, which is offset from the center of the transmission device, to the center of the viewing device and centered in the periphery of the images as projected onto the camera sensors. An interconnect optics assembly as described above is used to shift the images so that they overlap at the viewing device.

This invention allows easy and convenient stereoscopic viewing of regions inside the body or other inaccessible areas. It restores to the surgeon the same kind of three-dimensional image he had when he was doing "open surgery" and before two-dimensional video endoscopes became the preferred method of surgery.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENTS

Figures 1, 2, 3:
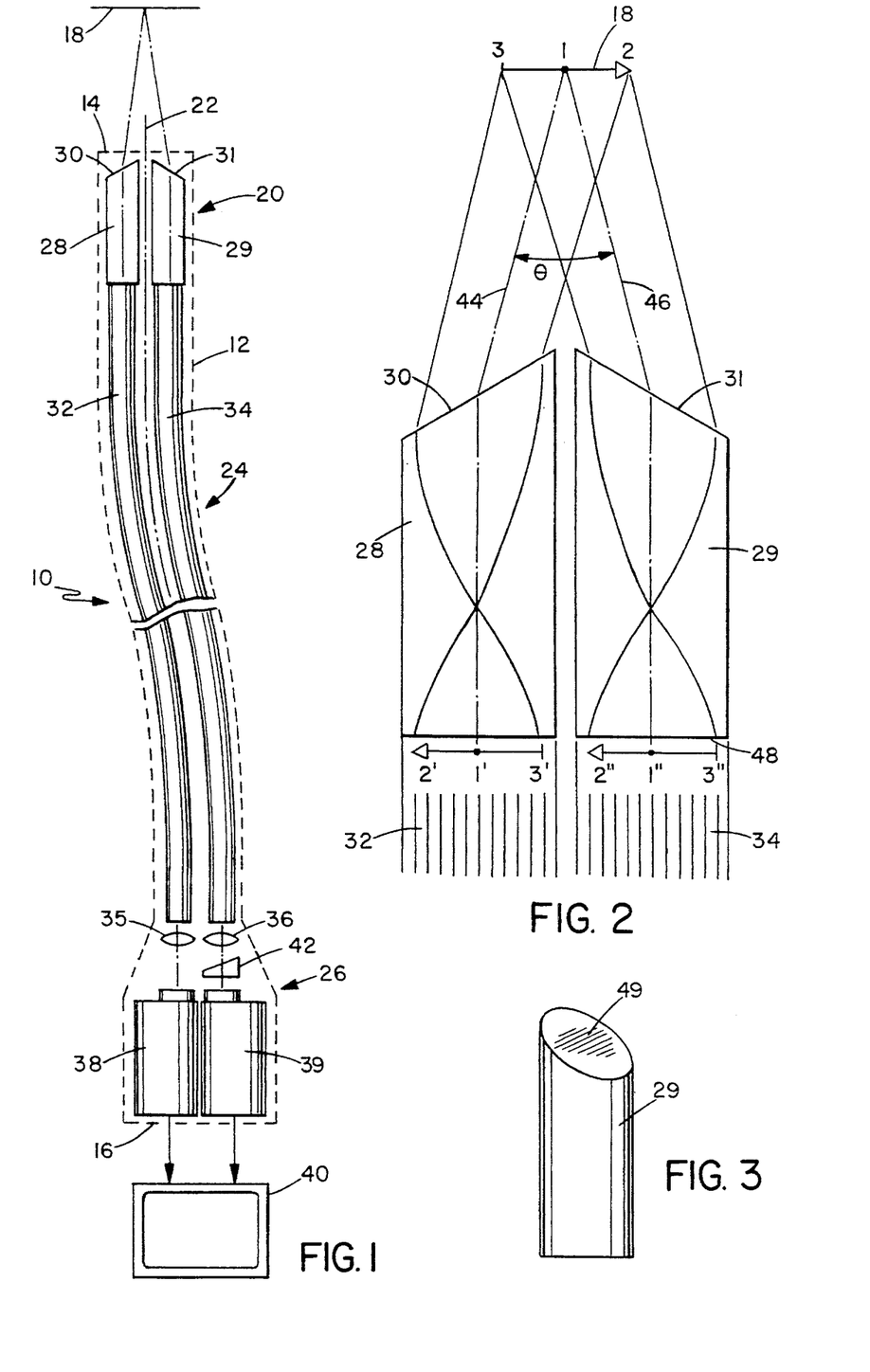
FIG. 1 is a schematic, side elevational view illustrating a three-dimensional endoscope system according to a first embodiment of the present invention.
FIG. 2 is an enlarged schematic view of the objective end of the system in FIG. 1, illustrating the light path through the lenses.
FIG. 3 is a side elevational view taken from the right-hand side in FIG. 1, illustrating one of the gradient index lenses with a modified cut end surface to provide a side-looking endoscope.

A three-dimensional or stereoscopic endoscope apparatus 10 according to a first embodiment of the present invention is schematically illustrated in FIGS. 1 and 2 of the drawings. As illustrated in FIG. 1, the apparatus 10 basically comprises an elongate sheath or tube 12 having a first end 14 for insertion into a body through an orifice or a surgical incision, and a second end 16 which remains outside the body. An optical system extends through the tube for providing separate right and left eye images of a region 18 under inspection. The system includes an image forming optical structure 20 at the first end of the tube 12 for forming two images of the object on opposite sides of the central axis 22 of the tube, an elongate optical transmission device 24 such as one or two bundles of optical fibers extending from the image forming structure 20 to the opposite end of the tube, and a viewing assembly 26 at the second end of the tube to enable viewing of the two images.

The tube 12 may be rigid or may comprise a flexible sheath. In the latter case, the transmission device 24 comprises one or more bundles of optical fibers, as in the illustrated embodiment. If the endoscope tube is rigid, the transmission device may comprise a rod lens or the like.

The image forming structure 20 in this embodiment comprises a pair of gradient index or GRIN lenses 28, 29 positioned with their axes parallel and one on each side of the central axis 22 of the system. The GRIN lenses are each provided with an angled or inclined end face 30, 31, respectively, facing the common object or region to be viewed. The angled faces are oriented so that the two lenses have their longest longitudinal dimensions positioned directly adjacent one another, as illustrated in FIGS. 1 and 2.

Each lens 28, 29 has a bundle 32, 34 of optical fibers extending from its rear end face through the endoscope tube. The bundles of optical fibers may be replaced with gradient index or GRIN rod lenses in a rigid endoscope apparatus.

Image viewing assembly 26 includes lenses 35, 36 at the exit end of the respective fiber-optic bundles, and a pair of miniature video cameras 38, 39 at the exit end of the endoscope for receiving the two images and converting them to right and left video images. The cameras are of the conventional type used in endoscope systems.

The surgeon or operator may view the images directly by looking into direct viewing eyepieces provided at the outer end of the endoscope. However, this may be inconvenient, and in the preferred embodiment of the invention the outputs of the two cameras are connected to a suitable stereo viewing device 40. Preferably, the stereo viewing device is the viewer as described in my U.S. Pat. No. 4,623,223, the contents of which are incorporated herein by reference. This viewer will allow the surgeon to view the images from the two cameras projected from a large concave mirror without having to use an eyepiece device. Conventional electronic techniques may be used to connect the video outputs of the two cameras to the viewer 40 where they are reflected onto angled mirrors for reflection onto the concave mirror, so that the viewer will see a three-dimensional, high quality image.

Preferably, an adjustment device 42 is provided in the image path between the exit end of one of the fiber-optic bundles and the video camera. This device is manually adjustable to alter the separation between the two images, allowing the viewer to adjust the image separation according to their own interpupillary eye distance and convergence ability. In the embodiment illustrated in FIG. 1, the adjustment device 42 comprises a single prism with its wedge positioned from right to left relative to the observer. The prism is movable towards and away from the exit end of the fiber-optic bundle via a suitable manual control (not illustrated). The angle of the prism will control the amount of image movement, and preferably a relatively shallow angle in the range of 10° to 12° is used, allowing fine control.

A suitable light source (not illustrated) will be provided in a conventional manner for illuminating a site within the body. The source may be external and connected to the internal end of the endoscope tube along a suitable light guide.

Gradient index or GRIN lenses have the property of forming a real image at their exit surface, rather than at a distance from the lens as with conventional lenses. Gradient index lenses have a varying refractive index with the refractive index being greatest at the center of the lens and gradually decreasing with radial distance outward from the center. Because of this, light rays passing through the center will travel more slowly than those further away from the optical axis. This causes the rays to travel in a sinusoidal path, arriving at the exit end of the lens at the same time.

By grinding and polishing angular end faces on the two GRIN lenses, the optical axes 44, 46 of the two images will converge at an angle Θ at object plane 18 at the desired working distance. The angled faces will redirect or converge the light rays from the object into two parallel image paths, as best illustrated in FIG. 2. Because light rays travel faster through the GRIN lenses at their outer edges than along the central axis of each lens, light rays from opposite sides of the object will all arrive at the exit plane or image plane 48 at the same time. Thus, considering the light rays emitted from positions 2, 1 and 3 on the object plane, it can be seen that the outermost rays 2 and 3 will have approximately equal path lengths to the image plane, and the central ray 1 will have a shorter path length. However, ray 1 travels through the center of the lens and thus will travel slower than the portions of rays 2 and 3 travelling through the lens, and images 2', 1', 3' and 2", 1", 3" are formed at the rear faces of the lenses.

As mentioned above, the angle of cut of the two lenses will be set according to the desired working distance and convergence angle. Where the two GRIN lenses are of ½ mm diameter, a 6° angle on each lens will converge an image of an object at a distance of 10 mm from the front of the lens.

The net effect of the angled surfaces and use of GRIN lenses is that two side-by-side images of the object under inspection will be produced at the rear faces of the lenses, and will be transmitted along parallel paths in the two fiber-optic bundles. At the proximal end of the fiber-optic bundles, the images are transmitted to the two miniature video cameras and from there to the viewer for 3-D viewing by a doctor or surgeon. The surgeon can adjust the image separation as discussed above by moving prism 42 towards or away from the exit end of the fiber-optic bundle.

Where the image forming device is to provide a sideways 3-D view out of the endoscope tube, as is the case with some endoscope arrangements, the end faces of the two GRIN lenses will be angled from front to rear as viewed in FIG. 1 as well as sideways. FIG. 3 is a side view of the lens 29 as illustrated in FIG. 1, illustrating a cut face 49 for side viewing of objects.

FIGS. 4–8 illustrate some alternative embodiments of the image forming device for use in the system illustrated in FIG. 1 in place of GRIN lenses 28 and 29. Some other parts of the endoscope in FIGS. 4–8 are equivalent to parts illustrated in FIGS. 1 and 2, and like reference numerals have been used where appropriate.

Figure 4:
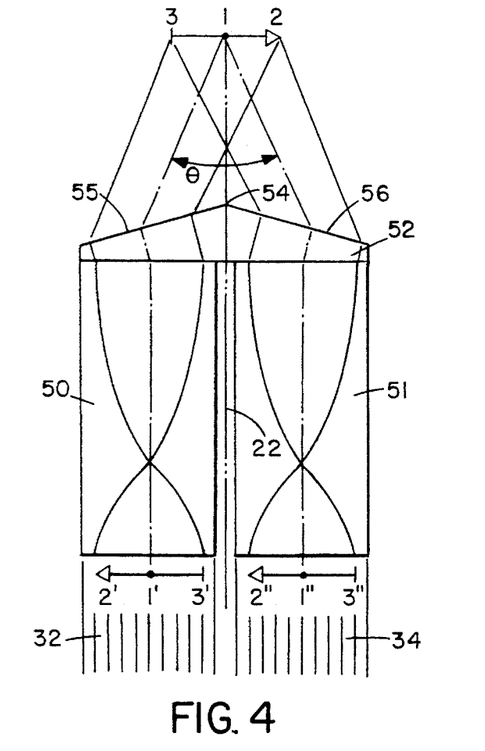
FIG. 4 is a view similar to FIG. 2 illustrating a modified image-forming optical arrangement according to another embodiment of the invention.

FIG. 4 illustrates an alternative in which two GRIN lenses 50 and 51 are positioned parallel to one another in the object viewing end of the endoscope tube, as in FIG. 1. However, instead of providing angled end faces directly on the lenses 50 and 51, the lens have standard flat end faces and a double prism 52 is cemented with its flat face against the outer end faces of lenses 50 and 51 and with its apex 54 located on the central axis 22 of the system. The angled faces 55, 56 of the prism have the same effect as the angled end faces 30, 31 of the GRIN lenses in the first embodiment and provide the desired convergence of the two images. The two images are transmitted along fiber-optic bundles 32, 34 as in the previous embodiment to be displayed in the 3-D viewer 40 or in a direct viewing or eyepiece device.

As in the previous embodiment, gradient index rod lenses may be used instead of the fiber-optic bundles for a rigid type endoscope. Also, a single fiber-optic bundle may replace the two bundles 32, 34 illustrated in FIGS. 1 and 4 to produce the right- and left-hand images in opposite halves of the bundle.

Figure 5:
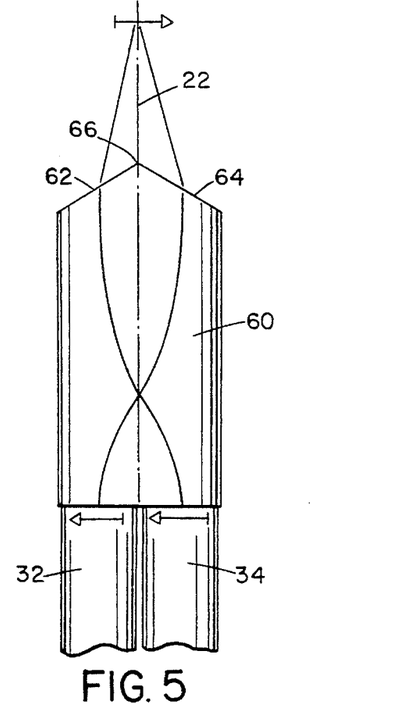
FIG. 5 is a view similar to FIGS. 2 and 4 illustrating another modified image-forming assembly.

FIG. 5 illustrates another alternative in which the two GRIN lenses are replaced with a single GRIN lens 60 having a prism cut end face with two angled surfaces 62, 64 meeting at apex 66 positioned on the central axis 22 of the endoscope. Instead of forming the angled surfaces on the GRIN lens itself, a prism may be cemented on the flat end of the GRIN lens, as in the embodiment of FIG. 4 but using only one GRIN lens instead of two.

In this version, the angled surfaces are cut at a relatively steep angle, with the angle between the surfaces at the apex being of the order of 100°. However, different angles may be used to provide different working distance. With a 100° angle, the steepness of the angled surfaces allows varying convergence with distance from the object by adjusting the focus at the camera eyepiece, for example. The two images will be formed in opposite halves of the GRIN lens at the exit end of the lens, where they will be inverted and reverted. The fiber-optic bundles 32, 34 will be cemented onto the respective halves of the end face in order to pick up and transmit the respective images. Instead of two separate fiber-optic bundles, a single, larger fiber-optic bundle may be used for the transmission path, with the images separated by any suitable means such as a prism or mirror at the proximal end of the path. The use of a single cylindrical lens instead of two such lenses has the advantage that the overall diameter of the endoscope tube can be reduced to a minimum. This is important in any medical instrument in order to reduce the size of any incisions and also reduce the risk of trauma to the patient.

Figure 6:
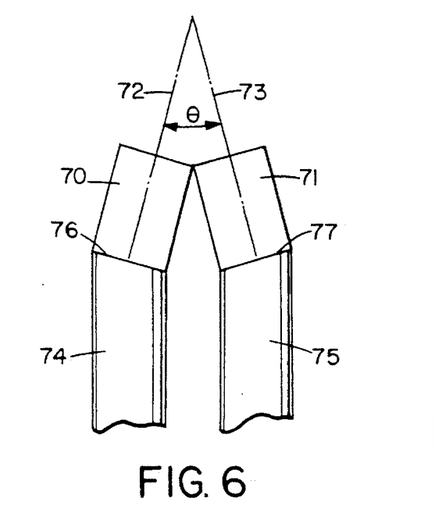
FIG. 6 is a view similar to FIGS. 2, 4 and 5 illustrating another alternative image-forming arrangement.

FIG. 6 illustrates another alternative in which two GRIN lenses 70, 71 are used which have flat end faces but which are angled with their optical axes 72, 73 tilted to provide the desired convergence angle Θ. The image transmission path is provided by two parallel fiber-optic bundles 74, 75 which have their end faces 76, 77 cut at an angle matching the end faces of the GRIN lenses so that they can be cemented in face to face abutment with the end faces of the GRIN lenses. Because the images from the GRIN lenses are automatically formed on the rear surfaces of the lenses, no focusing is required and the images will be transmitted intact to the other end of the fiber-optic bundles.

If a sideways or angled view of the object is needed, the GRIN lenses may be angled from front to rear as well as sideways, in a similar manner to the angled end face of the GRIN lens as illustrated in FIG. 3 above. The end faces of the attached fiber-optic bundles will be similarly angled for abutment with the rear end faces of the tilted lenses.

Figure 7:
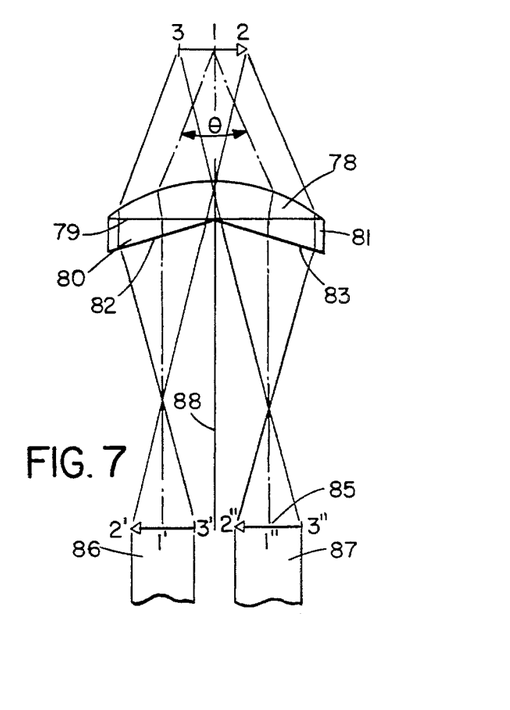
FIG. 7 is a schematic sectional view illustrating an image-forming optical assembly according to another embodiment of the invention.

FIG. 7 illustrates an alternative image forming device or objective lens system which does not use GRIN lenses. In the embodiment of FIG. 7, a single refractive or achromatic objective lens 78 is used to create two images of a single object from two converging angles. Two prisms 80, 81 are placed against or near the exit surface 79 of the objective lens with their thinnest ends abutting on the center line of the lens and the central axis 22 of the endoscope system. The prisms divide the lens into two halves, and the inclined surfaces 82, 83 of the prisms will act to diverge the optical axes of the two halves of the lens so that they are parallel to each other. As illustrated in the ray diagram of FIG. 7, the lens in combination with the prisms 80 and 81 will produce two images 2', 1', 3' and 2", 1", 3" at the image plane 85 a predetermined distance behind the lens. Two fiber-optic bundles 86, 87 are positioned with their ends at the image plane 85 to pick up the two images and transmit them to the opposite end of the endoscope tube for viewing, as in the embodiment of FIG. 1.

The lens as illustrated in FIG. 7 is plano-convex with its curved face directed towards the object. However, it may alternatively be biconvex or be positioned with its flat face outermost.

A light baffle 88 may optionally be placed between the two image paths along the central axis of the system in the same plane as the abutment of the two prisms, as illustrated in FIG. 7. This will reduce stray reflections in the two optical channels.

With this arrangement, right and left eye views of a common object are thus produced and may be utilized by two video cameras, as in FIG. 1, to transmit the right and left eye video pictures to a 3-D video viewer 40 or to a direct viewing eyepiece. Gradient index rod lenses may be used in place of the fiber-optic bundles in a rigid type endoscope. The image formed at the image plane 85 may also be transmitted with refractive relay lenses in a rigid-type endoscope to video cameras or to direct viewing eyepieces.

Figure 8:
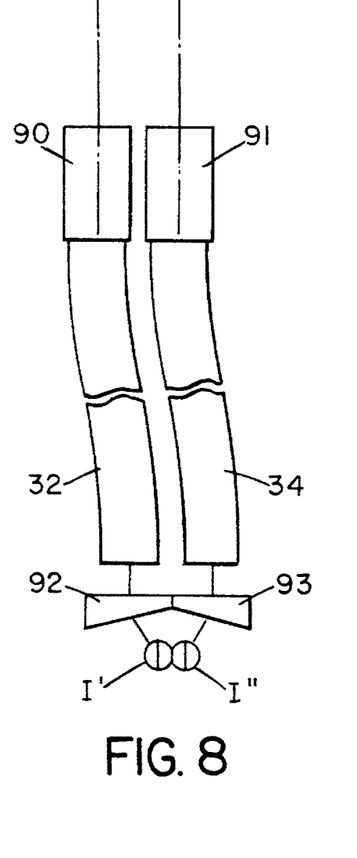
FIG. 8 illustrates a modified endoscope apparatus according to another embodiment of the invention.

In all of the above embodiments, the image forming device at the distal end of the endoscope had angled faces for converging the images. However, in some applications, GRIN lenses 90, 91 with flat end faces may be used, as illustrated in FIG. 8. The lenses 90, 91 are secured to respective fiber-optic bundles 32, 34 at their rear end faces, and any necessary adjustment for convergence is done by an adjustment device between the opposite ends of the fiber-optic bundles and the viewing device. Instead of a single prism in the path of one of the images, as in FIG. 1, the adjustment device illustrated in FIG. 8 comprises two identical or double diverging prisms 92, 93 which are offset 180° and positioned with their thinnest ends on central axis 22.

Figure 9A:
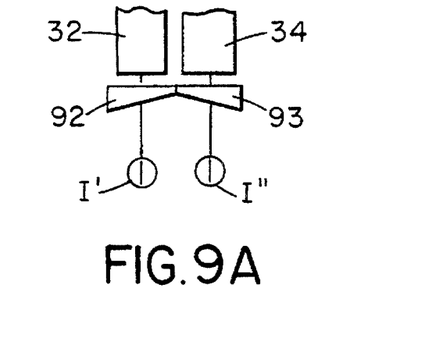
FIGS. 9A and 9B illustrate operation of the adjustment prisms of FIG. 8 to adjust the image separation.
Figure 9B:
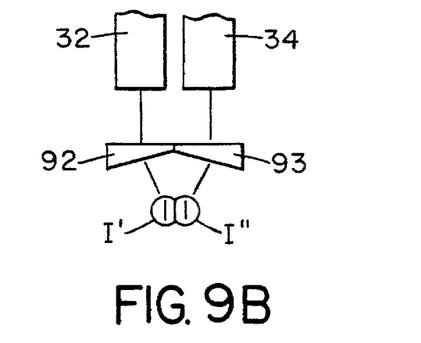

The operation of the two prisms is illustrated in FIGS. 9A and 9B. As the prisms 92, 93 are moved towards the ends of the fiber-optic bundles, the images I' and I" will move outwardly. As the prisms are moved away from the bundles in the opposite direction, the images will move inwardly towards each other. In effect, this will control the convergence of the images. The amount of deflection can be changed by varying the angles of the prisms. Preferably, the prism angles are relatively shallow to provide fine control. In a preferred embodiment of the invention, a prism angle of around 6° on each prism was used.

Double diverging prisms may also be used as the adjustment device in any of the previous embodiments to allow a user to adjust to their own interpupillary eye distance and greatest viewing comfort. The prisms are preferably cemented together and move together as a unit.

The use of either a single adjustable prism in the path of one of the images or double diverging prisms in the path of both images in any of the endoscope systems described above has the advantage of permitting individual adjustment of the image separation to the individual's own eyes and viewing preference.

Figure 10:
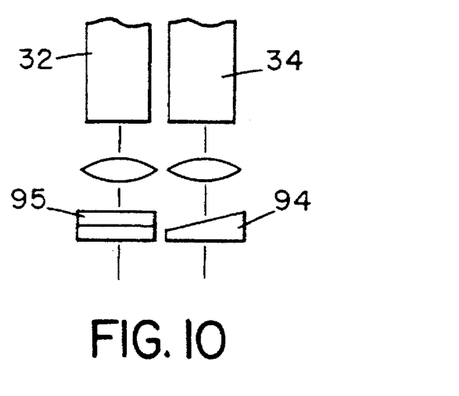
FIG. 10 illustrates an alternative adjustment device for adjusting the relative positions of the images.

In FIGS. 8 and 9, two prisms which are offset 180° are used in the respective image paths. FIG. 10 illustrates a modification of the adjustment device for use in situations where there may be some vertical drift between the two images, either where the cameras themselves have some drift, or where the GRIN lenses are not aligned correctly. In FIG. 10, a first prism 94 is provided at the exit end of one fiber-optic bundle with its thinnest end at the central axis. This prism will move the images towards and away from one another for horizontal alignment purposes. A second prism 95 is positioned at the exit end of the other fiber-optic bundle. Prism 95 is offset at 90° to the first prism. Movement of this prism towards and away from the fiber-optic bundle will shift the image vertically relative to the other image, for vertical alignment purposes.

Figure 11:
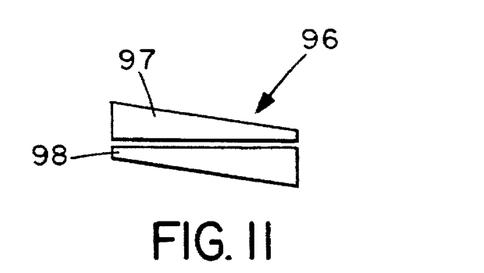
FIG. 11 illustrates another alternative image separation adjustment device.

FIG. 11 illustrates another alternative adjustment device 96 for adjustment of the image separation. This device may be used in any of the endoscope systems described above. Adjustment device 96 comprises two counter-rotating prisms 97, 98 positioned in closely parallel planes with their centers on the optical axis of one of the fiber-optic image-carrying bundles. They are arranged to rotate in opposite directions simultaneously with their points of overlapping matching a centerline of the line between the centers of the two GRIN lenses.

This arrangement is advantageous where there is little room between the fiber-optic bundles and the viewing cameras, since no axial movement of the adjustment device is required. As the prisms counter-rotate, the image will shift laterally. When both prisms are oriented with their thickest edges at the left as viewed in FIG. 11, the image will be deflected a maximum amount to the left. When both lenses are rotated through 180° from this position with their thickest edges at the right, the image will be deflected a maximum amount to the right. Between these two positions the image will travel in a straight line right to left with the minimum deflection of the image occurring at the ±90° position illustrated in FIG. 11. Counter-rotating prisms may be positioned in the path of one or both images. The amount of deflection can be changed by changing the angles of the prisms.

Figure 12:
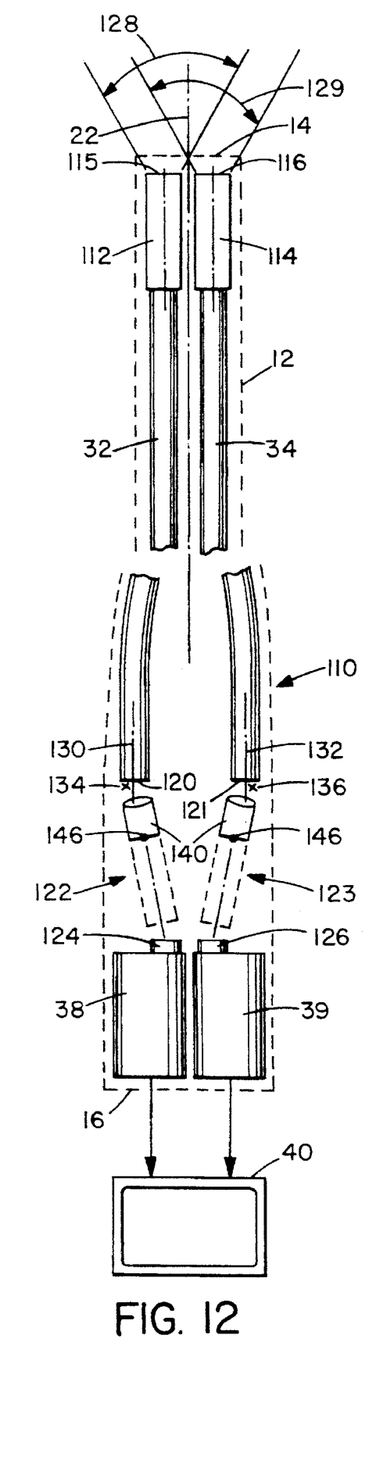
FIG. 12 is a schematic, side elevational view illustrating an endoscope apparatus according to another embodiment of the invention.

FIGS. 12–15 illustrate an endoscope apparatus 110 according to another embodiment of the invention, which avoids the need to grind angled end faces at the distal end of the endoscope. Some parts of the apparatus in FIG. 12 are identical to parts in the first embodiment of FIG. 1, and like reference numerals have been used for like parts as appropriate. The apparatus 110 basically comprises an elongate tube or housing 12 having a first or distal end 14 for insertion into a body through an orifice or surgical incision, and a second or proximal end 16 which remains outside the body. An optical system extends through the tube for providing separate right- and left-hand images of a region under inspection. The optics at the distal end of the tube comprises two separate right- and left-hand imaging lenses 112,114 arranged in a contiguous side-by-side parallel configuration. For compactness, the optical axes are parallel and non-converging. The lenses 112,114 each have a flat or planar distal end surface 115,116, respectively, facing the region to be viewed.

In the preferred embodiment of the invention, lenses 112,114 are gradient index or GRIN lenses, although other types of lenses such as ball lenses or traditional refractive lenses may be used. From a distance of about 40 lens diameters or more, the fields of view of the right and left images will overlap sufficiently so that the unaided eyes of the average person can converge the images to obtain "fusion" and a three-dimensional picture. With opto-mechanical systems, such as video, this becomes more difficult. In a small diameter endoscope system, where the lenses are of around ½ mm diameter, it is necessary to accomplish a working distance of 3–5 mm from the distal end of the endoscope. To do this, a convergence angle between the right and left eye views of the order of 12° is necessary for comfortable viewing. The optics between the lenses 112,114 and the cameras 38,39 achieves this objective.

Two bundles 32,34 of imaging fibers extend from the inner end of each lens 112,114, respectively, towards the proximal end of the tube 12. The proximal ends 120,121 of the fiber bundles 32,34 are spaced from the proximal end of the tube, in which a pair of miniature video cameras 38,39 are positioned for receiving the right- and left-hand images. An interconnect optics assembly 122,123 for offsetting the images onto the center lines of the respective video camera sensors 124,126 extends from the proximal ends 120 of the fiber bundles to the camera sensors. The outputs of the two cameras are preferably connected to a stereo viewing device 40 as described above in connection with the first embodiment of the invention.

The endoscope tube must be of very small diameter since it must be insertable into the body through a relatively small incision or opening, and thus the lenses 112,114 and fiber optic bundles must also be of very small diameter. In one embodiment of the invention, GRIN lenses having a diameter of 0.020" were used, while the imaging fiber bundles were of the same diameter and each contained 10,000 individual glass fibers which were carefully assembled so that the distal and proximal ends matched exactly.

Although fiber optics bundles 32,34 are used to transmit the images from the objective lenses 112,114 to the proximal end of the endoscope in the preferred embodiment, a rigid endoscope may alternatively use rod lenses or traditional refractive lenses to convey the images, as in the previous embodiments.

Figure 13A:
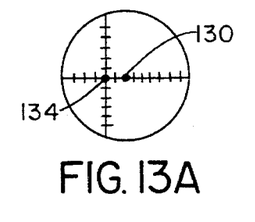
FIGS. 13A and 13B are schematic illustrations of the images of a cross hair produced at the proximal end of the fiber bundles on the left- and right-hand side of the endoscope of FIG. 12, respectively.
Figure 13B:
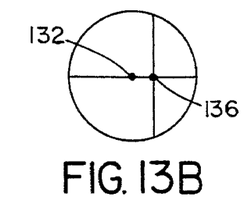

The fields of view 128,129, respectively, of an image centered on the central axis 22 of the system in the left eye and right eye optical systems of the endoscope are offset to the left and right, respectively, of the center axis 130,132 of that system. The imaging fiber bundles 32,34 transmit these offset images to the proximal ends 120 of the bundles, where they form offset images having centers 134,136, respectively, which are offset from the center lines 130,132 of the respective imaging fiber bundles, as illustrated in FIGS. 12, 13A and 13B. The interconnect optics assemblies 122,123 for the left- and right-hand images are designed to magnify and project the images so that their centers are centered on the camera sensors 124,126, respectively, rather than being offset. The right and left images as seen by optics at the distal end of the endoscope are presented on two separate LCD's or CRT's, and the LCD's or CRT's are incorporated into a suitable 3-D viewer such as that described in my U.S. Pat. No. 4,623,223 referred to above.

Figures 15, 17, 18, 19:
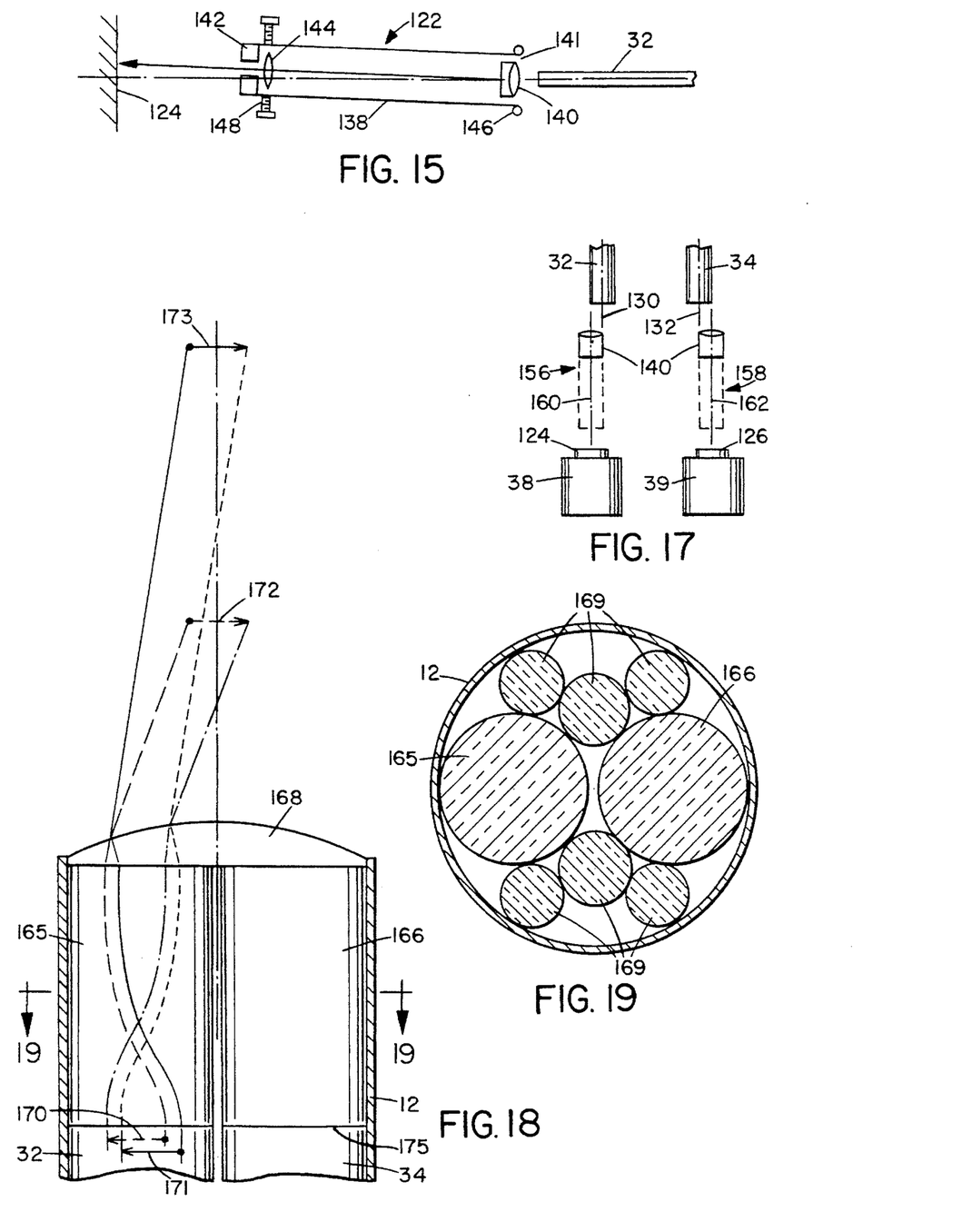
FIG. 15 is a more detailed schematic illustration of the interconnect optics assembly on one side of the endoscope of FIG. 12.
FIG. 17 illustrates another alternative interconnect optics assembly.
FIG. 18 is a view similar to FIGS. 2 and 4 illustrating a modified image-forming optical arrangement according to another embodiment of the invention.
FIG. 19 is a sectional view on the lines 19—19 of FIG. 18.

The interconnect optics assembly 122 for the left-hand optical system is illustrated in more detail in FIG. 15. It will be understood that the right eye interconnect assembly 123 will be identical. Assembly 122 is arranged to focus on the proximal end 120 of the imaging fibers 32. Assembly 122 transmits the image at that end as an enlarged focused image onto the sensor surface 124 of the camera. Each interconnect optics assembly basically comprises a tubular housing 138 having a first, achromatic lens 140 mounted at one end 141 of the housing. Lens 140 is focussed on the proximal end 120 of the respective fiber bundle. A lightstop 142 is located at the opposite end of the housing, with a field lens 144 adjacent lightstop 142. Field lens 144 and lightstop 142 have been omitted in FIG. 12 for clarity. Housing 138 is pivotally mounted in the endoscope tube via a four-way pivot at pivot point 146 at the first end 141 of the housing, as illustrated schematically in FIG. 15. The pivot mechanism is arranged to allow a pivot of up to 6° from central axis 137. Pivot screws 148 set at 90° intervals allow angular adjustment of housing 138.

Figure 14A:
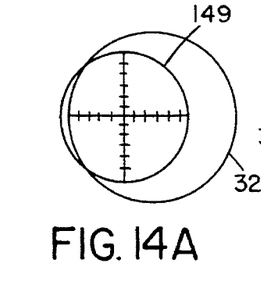
FIGS. 14A and 14B are schematic illustrations of the images as offset by the interconnect optics assembly of FIG. 12.
Figure 14B:
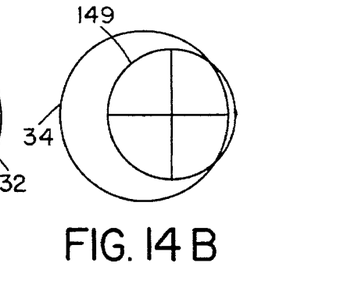

Pivoting of each interconnect optics assembly will deflect the image from the proximal end of the fiber bundle to the center of the respective camera sensor 124,126. The center 134,136 of the offset image is placed on the center line of the interconnect optics assembly 122,123 by pivoting the center line at or near the first lens 140. Lightstop 142 will define the periphery 149 of the image, as illustrated in FIGS. 14A and 14B. Pivoting of the housing 138 about pivot point 146 via adjustment screws 148 will deflect this image. By viewing the image received by the camera sensors in the left and right LCD's of the 3-D viewer while adjusting screws 148, the interconnect optics can be adjusted so that the images appear centered to each other on the respective LCD's. When this occurs, the right eye and left eye images will be "fused" in the brain and a single three-dimensional image will be seen in the 3-D viewer as described in U.S. Pat. No. 4,623,223. When viewed in the 3-D viewer, the images will appear to be superimposed by the optical system in the 3-D viewer, forming a single three-dimensional stereoptic image. The two images may also be alternated on a single CRT or LCD for use with alternating image glasses or in an alternating image mode without the use of alternating image glasses.

The light stop 142 has the function of reducing the field of view to take out the peripheral edge of the fiber optic bundle. However, this is not essential since this edge will not normally be apparent to the viewer, and the viewer's brain will fill in the missing parts as is readily done in practice during normal vision.

Figure 16:
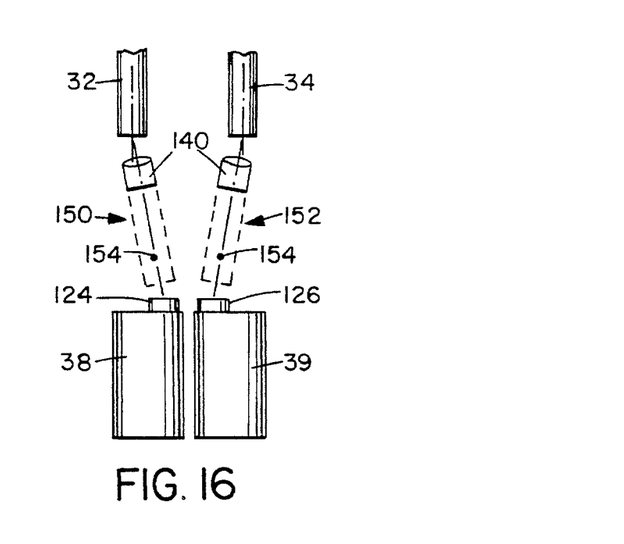
FIG. 16 illustrates an alternative interconnect optics assembly for use with the endoscope of FIG. 12.

FIGS. 16 and 17 illustrate two alternative techniques for adjustably offsetting the image between the proximal ends of the fiber bundles and the camera sensors. In FIG. 16, right- and left-hand interconnect optics devices 150,152 are provided which are equivalent to that of FIG. 15 except that the tubular housing of each device is pivoted at a different four-way pivot point 154. The interconnect optics devices in FIG. 16 are otherwise identical to that of FIGS. 12 and 15, and like reference numerals are provided for like parts as appropriate. The location of the pivot point in FIG. 16 at a greater distance from lens 140 will result in larger movement of lens 140 with a smaller angular movement of the housing. Thus, very little movement of the adjustment screws will be required in this version. However, this may make it harder to control the image match-up than in the version of FIG. 14, and will result in some loss of field of view as the achromatic lenses 140 move farther off center relative to the imaging fibers. By pivoting at or close to the achromatic lenses 140 as in the previous embodiment, the lenses will stay essentially on or close to the center, reducing field of view loss, and the adjustments will be less sensitive in controlling image match up. It will be understood that the angular movement illustrated in FIGS. 12 and 16 is greatly exaggerated, since the actual tilt of the housing will normally be about 6°.

FIG. 17 illustrates another alternative in which left and right-hand interconnect optics devices 156,158 are provided which are movable in a direction transverse to the center line of the respective fiber optic bundle so that the center line 160,162 of the respective interconnect optics device is offset to match the offset image at the proximal end of the fiber optic bundle. The interconnect optics devices of FIG. 17 are otherwise identical to that of FIGS. 12 and 15, and like reference numerals have been used for like parts, as appropriate.

Thus, the interconnect optics devices of FIGS. 12 to 17 allow the adjustment in the image to the center of the camera sensors to be made at the proximal end of the endoscope, between the imaging fibers and the camera sensors, and allow the GRIN lenses to have flat, planar end faces 115,116 rather than angled faces as in FIG. 1. The grinding and polishing of a single planar surface is much easier and less costly than angular wedges or prisms with two surfaces.

FIGS. 18 and 19 illustrate a modified image-forming objective lens assembly for use at the distal end of an endoscope in place of angled GRIN lenses 28,29 of FIG. 1. The image-forming assembly of this embodiment comprises a pair of objective lenses 165,166 arranged in a contiguous, side-by-side and parallel configuration, the lenses 165,166 having flat end faces, and a plano-convex lens 168 covering the end faces of both imaging lenses. As in the previous embodiments, fiber optics imaging bundles 32,34 are cemented to the proximal ends of each lens 165,166. The lenses 165, 166 are preferably GRIN lenses, although other types of lenses such as ball lenses or traditional refractive lenses may be used.

Lighting fibers 169 extend along opposite sides of the two, side by side lenses 165,166 to the proximal end of the endoscope tube for connection to a suitable light source. The plano-convex lens covers both the imaging lenses 165,166 and the lighting fibers 169. Lighting fibers may also be used in this way in any of the previous embodiments in order to illuminate the object.

The spherical surface of the plano-convex lens will converge both the imaging axes and the lighting fibers to a common point of focus at the working distance. The spherical surface will converge light in a similar manner to a field lens. It is, in effect, a spherical prism. If it is located with its plano surface contiguous to the outer or distal end surfaces of the GRIN lenses, as illustrated, it will shorten the working distance, depending on the convex radius. FIG. 18 illustrates the formation of images 170,171 at the proximal end 175 of the left hand GRIN lens 28 of objects 172,173 positioned at a shorter distance and longer distance, respectively, from the lens 168. This shows that the image shifts outward from the center as the working distance decreases. Therefore the convergence angle between the eyes increases as the object or working distance decreases, in other words this provides an automatic convergence correction for working distance. The image shift with decreasing working distance moves the right- and left-hand images farther apart on the viewer as the working distance decreases, requiring a somewhat greater convergence angle between the eyes. However, the eyes can automatically make this adjustment just as they do in normal stereoscopic vision.

One advantage of using a plano-convex lens as illustrated in FIG. 18 is that it is easier, less costly, and more secure than an unprotected plano lens surface as in FIG. 12, for example. In the embodiment of FIG. 12, the GRIN lens surfaces and the lighting fiber end surfaces are exposed to abrasion as well as to cleaning and disinfecting chemicals. The lenses and light fibers are encapsulated only in epoxy, which is softer and considerably less durable than a glass lens surface. With the arrangement of FIG. 18, the plano-convex lens therefore acts as a lens cover protecting the ends of the lighting fibers and the GRIN lenses. Although the plano-convex lens is positioned with its plano surface contiguous to the end surfaces of the GRIN lenses in the preferred embodiment, it may alternatively be used with the plano side facing the object plane. This has the advantage of reducing reflections from the lighting fibers.

In the embodiment of FIG. 18, a suitable adjustment device may be provided between the proximal ends of fiber bundles 32,34 and the video cameras, as in the previous embodiments, or an interconnect optics device as in any of FIGS. 12,15,16 or 17 may be used in conjunction with this version for increased adjustability.

The endoscope devices described above will provide a clear 3-D image of a site within the body. By using the endoscopes with a 3-D viewer as described in U.S. Pat. No. 4,623,223 referred to above, the user will need no special glasses to see the display in stereo or three dimensions. This will enhance the usefulness of the endoscopes as diagnostic and surgical tools. The adjustment prism or prisms at the exit end of the fiber-optic image-carrying bundles allow the user to introduce their own viewing preference, including interpupillary distance.

Although the above embodiments are described in connection with an endoscope instrument as used in the medical field to view internal regions of the body, it will be understood that this apparatus can also be used to view other inaccessible areas which are not directly viewable by eye, such as machinery, pipes, bores and the like.

Although some preferred embodiments of the invention have been described above by way of example only, it will be understood by those skilled in the field that modifications may be made to the disclosed embodiments without departing from the scope of the invention, which is defined by the appended claims.

I claim:

1. An endoscope apparatus for viewing visually obscured areas, comprising:

an elongate endoscope tube having a central longitudinal axis, a first end for insertion into a visually obscured area, and an opposite second end which remains outside the visually obscured area;

an optical image-forming device in the first end of the endoscope tube for forming two images of an object along converging axes on opposite sides of said central axis;

the image-forming device including a pair of optical surfaces each cut at a predetermined angle relative to said central axis, whereby the surfaces are directed at different angles relative to the object, the optical surfaces being arranged to direct the images into closely adjacent, parallel optical paths;

an elongate optical transmission device extending through the endoscope tube from said image-forming device for transmitting the images to the second end of the tube; and stereoscopic viewing means for receiving and viewing the two images.

2. The apparatus as claimed in claim 1, wherein the optical transmission device comprises at least one bundle of optical fibers.

3. The apparatus as claimed in claim 2, wherein the optical transmission device comprises two bundles of optical fibers extending side by side through the endoscope tube, each bundle comprising means for receiving and transmitting a respective one of the two images.

4. The apparatus as claimed in claim 1, wherein the optical image-forming device comprises a single, image converging lens having at least one curved, convex face, and a pair of image diverging members placed at the exit face of said lens for diverging two images of an object formed by said lens into parallel, closely adjacent paths, the diverging members having said angled optical surfaces.

5. The apparatus as claimed in claim 4, wherein said lens comprises a plano-convex lens having a convex face facing outwardly and an opposite, flat face.

6. The apparatus as claimed in claim 5, wherein said image converging members comprise a pair of prisms each having a flat face placed in alignment with a respective half of said flat face of the lens, and having angled surfaces tapering inwardly towards the center of the lens.

7. The apparatus as claimed in claim 1, wherein the optical image-forming device comprises at least one gradient index lens.

8. The apparatus as claimed in claim 7, wherein the image forming device comprises a single gradient index lens with an end face facing the object having a double wedge prism shape with an apex on the central axis, said angled optical surfaces comprising the angled faces of the prism, and comprising means for forming two images of the object at an exit face of said lens, said transmission device being secured to the exit face of said lens.

9. The apparatus as claimed in claim 7, wherein the image forming device comprises a pair of gradient index lenses arranged parallel to one another on opposite sides of said central axis, the lenses having opposite flat entry and exit faces, and a double wedge prism having a flat face secured across the flat entry end faces of the lenses and having an apex lying on said central axis.

10. The apparatus as claimed in claim 7, wherein the image forming device comprises a single gradient index lens having a central axis lying on the central axis of the endoscope tube, the lens having opposite flat entry and exit faces, and a double wedge prism having a flat face secured to the flat entry end face of the lens and angled faces meeting at an apex lying on the central axes of the lens and endoscope tube.

11. The apparatus as claimed in claim 7, wherein the optical transmission device has a first end secured to the rear face of the gradient index lens.

12. The apparatus as claimed in claim 7, wherein the image forming device comprises a pair of gradient index lenses having end faces angled relative to the central axis.

13. The apparatus as claimed in claim 12, wherein the lenses are positioned parallel to one another on opposite sides of said central axis, and each have angled end faces converging towards the central axis with the longest dimension sides of the two lenses being positioned adjacent one another.

14. An endoscope apparatus for viewing visually obscured areas, comprising:

an elongate endoscope tube having a central longitudinal axis, a first end for insertion into a visually obscured area, and an opposite second end which remains outside the visually obscured area;

an optical image-forming device in the first end of the endoscope tube for forming two images of an object along converging axes on opposite sides of said central axis;

the image-forming device including a pair of gradient index lenses having end faces angled relative to the central axis for directing the images into closely adjacent, parallel optical paths, the lenses being tilted relative to the central axis;

an elongate optical transmission device extending through the endoscope tube from said image-forming device for transmitting the images to the second end of the tube, the transmission device comprising a pair of parallel image transmitting members each having an end face angled for face-to-face abutment with the tilted exit end face of the respective lenses; and stereoscopic viewing means for receiving and viewing the two images.

15. An endoscope apparatus for viewing a visually obscured area not directly viewable, comprising:

an elongate endoscope tube having a central longitudinal axis, a first end for insertion into a visually obscured area, and a second end which remains outside the visually obscured area;

an optical image forming device in the first end of the endoscope tube for forming right and left images of an object on closely adjacent, parallel paths;

an elongate optical transmission device having opposite first and second ends and extending through the endoscope tube from the image forming device for transmitting the images to the second end of the transmission device;

stereoscopic viewing means for receiving the images from the second end of the transmission device; and adjustment means between the second end of the transmission device and the viewing means for adjustment of the separation between the two images.

16. The apparatus as claimed in claim 15, wherein the adjustment means comprises at least one prism located in the path of one of the images and adjustment means for moving the prism towards and away from the second end of the transmission device.

17. The apparatus as claimed in claim 15, wherein the adjustment means comprises a pair of prisms located in the respective image paths.

18. The apparatus as claimed in claim 17, wherein one of the prisms is offset 180° from the other prism.

19. The apparatus as claimed in claim 17, wherein one of the prisms is offset 90° from the other prism.

20. The apparatus as claimed in claim 15, wherein the adjustment means comprises a pair of counter-rotating prisms located in the path of one of the images.

21. The apparatus as claimed in claim 15, wherein the image-forming device includes a pair of optical surfaces on opposite sides of said central axis each cut at a predetermined angle relative to said central longitudinal axis for directing the images into closely adjacent, parallel optical paths.

22. The apparatus as claimed in claim 21, wherein the image-forming device comprises at least one gradient index lens.

23. The apparatus as claimed in claim 15, wherein the optical image forming device comprises two imaging lenses arranged side-by-side in a contiguous, parallel configuration.

24. The apparatus as claimed in claim 23, wherein the imaging lenses have flat, planar end faces facing the object.

25. The apparatus as claimed in claim 23, wherein the lenses are GRIN lenses.

26. The apparatus as claimed in claim 15, wherein the stereoscopic viewing device comprises a stereoscopic viewer for viewing the left and right images simultaneously.

27. An endoscope apparatus for viewing a visually obscured area not directly viewable, comprising:

an elongate endoscope tube having a central longitudinal axis, a first end for insertion into a visually obscured area, and a second end which remains outside the visually obscured area;

an optical image-forming device in the first end of the endoscope tube for formnig right and left images of an object on closely adjacent, parallel paths;

an elongate optical transmission device having opposite first and second ends and extending through the endoscope tube from the image forming device for transmitting the images to the second end of the transmission device;

stereoscopic viewing means for receiving the images from the second end of the viewing device; and adjustment means between the second end of the transmission device and the viewing means for adjustment of the separation between the two images, including first and second interconnect optics assemblies extending from the second end of the optical transmission device towards the second end of the endoscope tube in the path of the left and right images, respectively, each interconnect optics assembly including at least one lens focussed on the second end of the optical transmission device for transmitting one of the images as a magnified image, and the adjustment means comprising means for moving the lens to shift the image.

28. The apparatus as claimed in claim 27, wherein the adjustment means comprises pivot means for pivoting the lens.

29. The apparatus as claimed in claim 27, wherein the lens has a central axis and the adjustment means comprises means for moving the lens transversely relative to the central longitudinal axis of the apparatus in order to-offset the central axis of the lens sideways.

30. The apparatus as claimed in claim 27, wherein the interconnect optics assembly includes a light stop for limiting the field of view of the final transmitted image.

31. An endoscope apparatus for viewing a visually obscured area which is not directly viewable by eye, comprising:

an elongate endoscope tube having a central longitudinal axis, a first, distal end for insertion into a visually obscured area, and a second, proximal end which remains outside the visually obscured area;

an optical image-forming device in the distal end of the endoscope tube for forming separate left and right images of an object;

an elongate optical transmission device having opposite proximal and distal ends and extending from the image-forming device through the endoscope tube towards the proximal end of the tube for transmitting the images along the tube;

stereoscopic viewing means for receiving and viewing the two transmitted images, each transmitted image having an image axis; and image converging means between the distal end of the endoscope tube and the stereoscopic viewing means for converging the images to provide a convergence angle between the left and right eye views in the viewing means.

32. The apparatus as claimed in claim 31, wherein the optical image forming device comprises first and second image-forming objective lenses arranged side-by-side in a parallel contiguous configuration and having distal end faces facing the object to be viewed.

33. The apparatus as claimed in claim 32, wherein the distal end faces of the objective lenses are flat.

34. The apparatus as claimed in claim 33, including a plano-convex lens positioned to cover the distal end faces of the objective lenses, the plano-convex lens comprising said image converging means.

* * * * *